(12) United States Patent
Vandendriessche et al.

(10) Patent No.: US 7,238,346 B2
(45) Date of Patent: Jul. 3, 2007

(54) HIGH CAPACITY RECOMBINANT ADENOVIRAL VECTOR FOR TREATMENT OF HEMOPHILIA A

(75) Inventors: Thierry Vandendriessche, Korbeek-Lo (BE); Marinee Chuah, Korbeek-Lo (BE); Stefan Kochanek, Cologne (DE); Gudrun Schiedner, Cologne (DE)

(73) Assignee: Vlaams Interuniversitair Instituut voor Biotechnologie VZW, Zwijnaarde (BE)

( * ) Notice: Subject to any disclaimer, the term of this patent is extended or adjusted under 35 U.S.C. 154(b) by 647 days.

(21) Appl. No.: 10/191,760

(22) Filed: Jul. 8, 2002

(65) Prior Publication Data

US 2004/0005293 A1 Jan. 8, 2004

(51) Int. Cl.
*A61K 48/00* (2006.01)
*C12N 15/861* (2006.01)

(52) U.S. Cl. .................. 424/93.2; 435/320.1; 435/456; 514/44

(58) Field of Classification Search ............. 435/320.1, 435/455, 456; 424/93.2
See application file for complete search history.

(56) References Cited

FOREIGN PATENT DOCUMENTS

WO  WO 97/45550 A2 * 12/1997

OTHER PUBLICATIONS

Connelly et al., "Complete short-term correction of canine hemophilia A by in vivo gene therapy," Blood 88 (10): 3846-3853, 1996.*
Reddy et al., "Sustained human factor VIII expression in hemophilia A mice following systemic delivery of a gutless adenoviral vector," Mol. Ther. 5 (1): 63-73, Jan. 2002.*
Gallo-Penn et al., "Systemic delivery of an adenoviral vecotr encoding canine factor VIII results in short-term phenotypic correction, inhibitor development and biphasic liver toxicity in hemophilia A dogs," Blood 97 (1): 107-113, Jan. 1, 2001.*
Balague et al., "Sustained high-level expression of full-length human factor VIII and resoration of clotting activity in hemophiliac mice using a minimal adenovirus vector," Blood 95: 820-828, 2000.*
Brown et al., "Helper-dependent adenovirus delivery of a canine FVIII B-domain deleted transgene in murine and canine models of hemophilia A," Blood 98 (11, pt. 1): 695a-696a, Nov. 16, 2001.*
VandenDriessche et al., "Viral vector-mediated gene therapy for hemophilia," Curr. Gene Ther. 1 (3): 301-315, Sep. 2001.*
Brown et al., "Helper-dependent adenoviral vectors mediate therapeutic factor VIII expression for several months with minimal accompanying toxicity in a canine model for sever hemophilia A," Blood 103 (3): 804-810, Feb. 1, 2004.*
Chuah et al., Therapeutic factor VIII levels and negligible toxicity in mouse and dog models of hemophilia A following gene therapy with high-capacity adenoviral vectors, Blood, Mar. 1, 2003, pp. 1734-1743, vol. 101, No. 5.
Linthout et al., Effect of Promoters and Enhancers on Expression, Transgene DNA Persistence, Hepatotoxicity After Adenoviral Gene Transfer the Human Apolipoprotein A-I, Human Gene Therapy, May 1, 2002, pp. 829-840, vol. 13.
VandenDricsche et al., Gene therapy for hemophilia A using oncoretroviral, lentiviral and gutless adenoviral vectors, Abstract, 9th Meeting of the European Society of Gene Therapy, Nov. 2-4, 2001, Antalya, Turkey, cover page, p. 3 and p. 26.
Presentation, Adenoviral Vectors, presented Nov. 2, 2001.
Brown et al., Helper-dependent adenovirus delivery of a canine FVIII B-domain deleted transgene in murine and canine models of hemophilia A, Abstract, Blood, Nov. 16, 2001, pp. 695a-696a, vol. 98, No. 11.
Brown et al., Helper-dependent adenoviral vectors mediate therapeutic factor VIII expression for several months with minimal accompanying toxicity in a canine model of severe hemophilia A, Blood, Feb. 1, 2004, pp. 804-810, vol. 103, No. 3.
Chuah et al., Biosafety of Adenoviral Vectors, Current Gene Therapy, 2003, pp. 1-7, vol. 3, No. 6.
High et al., Immune Response to AAV and to Factor IX in a Phase I Study of AAV-Mediated, Liver-Directed Gene Transfer for Hemophilia B, Molecular Therapy, May 2004, pp. S383-S384, vol. 9, Supplement 1.
Raper et al., Fatal systemic inflammatory response syndrome in a ornithine transcarbamylase deficient patient following adenoviral gene transfer, Abstract, Molecular Genetics and Metabolism, Sep.-Oct. 2003, pp. 148-158, vol. 80.

* cited by examiner

*Primary Examiner*—Scott D. Priebe
(74) *Attorney, Agent, or Firm*—TraskBritt

(57) ABSTRACT

The invention relates to adenoviral vectors. More particularly, this invention relates to recombinant high capacity adenoviral vectors which can be employed in the treatment of hemophilia A, as well as methods and process for their creation and use.

5 Claims, 8 Drawing Sheets

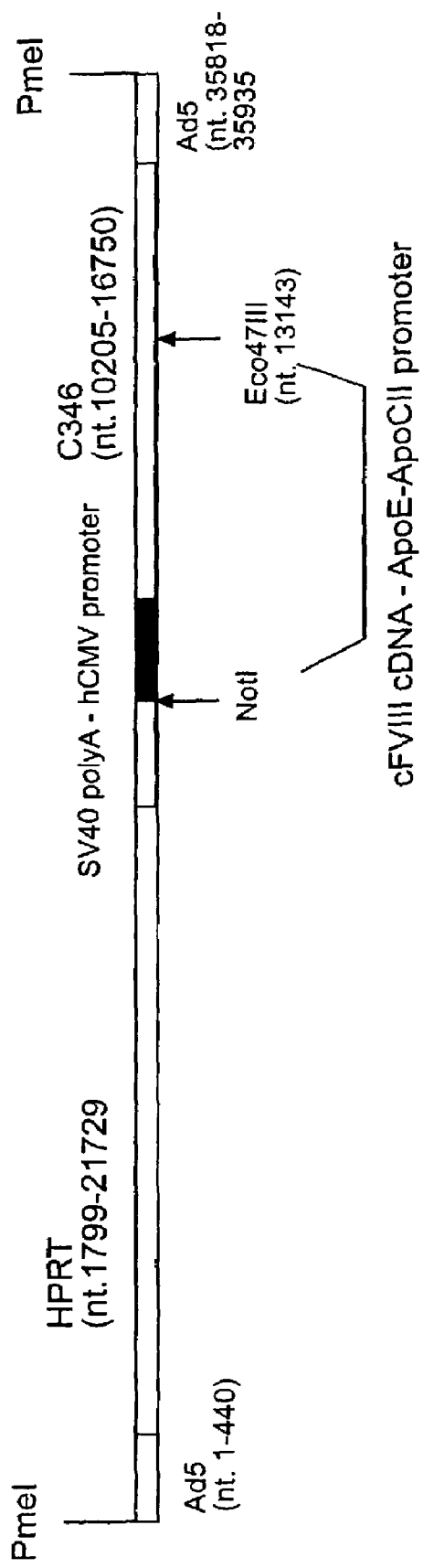

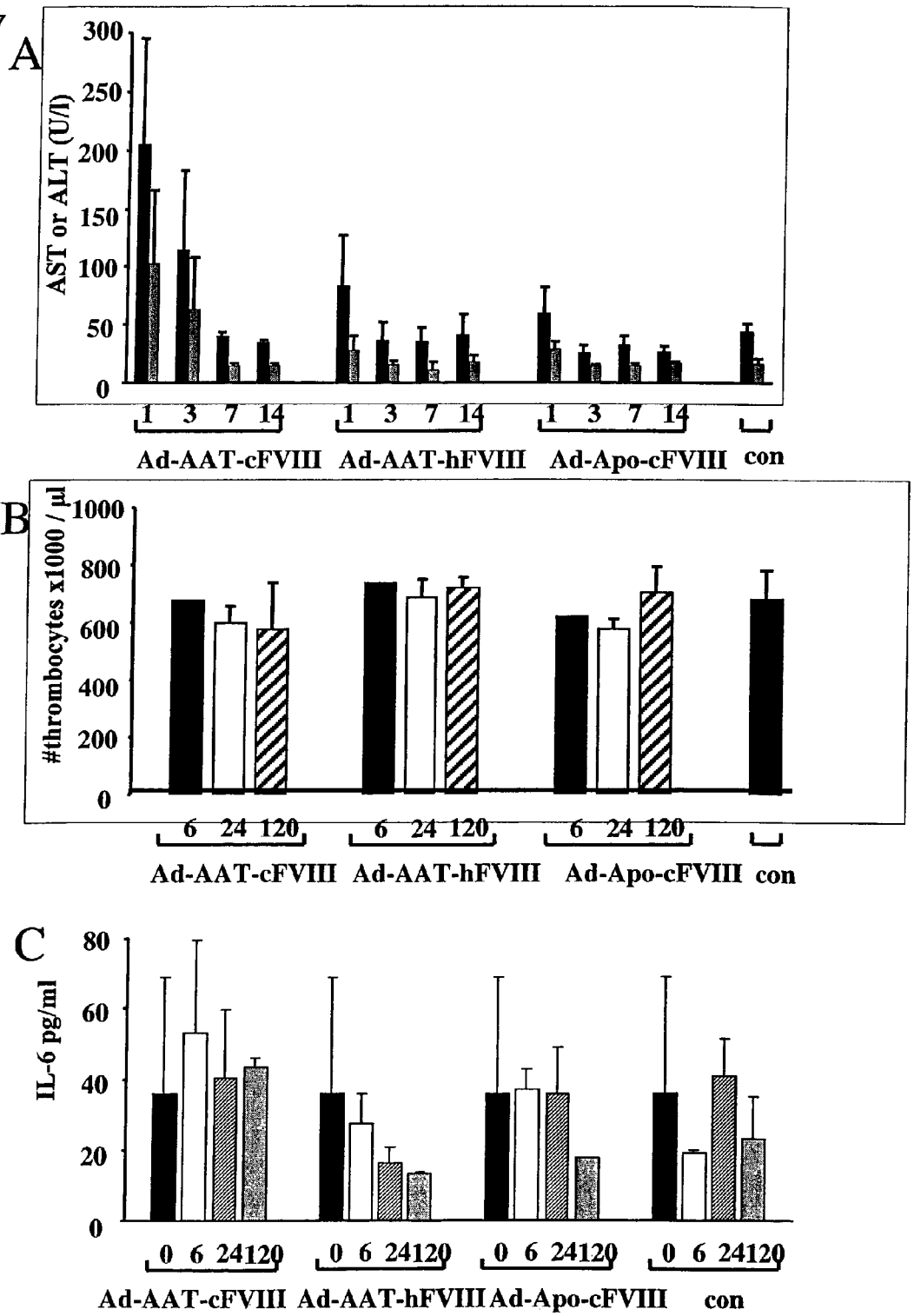

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:

```
<223> OTHER INFORMATION: PCR primer

<400> SEQUENCE: 1
ccatataaca tctaccctca                                               20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
gtttctcctg agaatgggaa                                               20
```

HIGH CAPACITY RECOMBINANT ADENOVIRAL VECTOR FOR TREATMENT OF HEMOPHILIA A

FIELD OF THE INVENTION

The invention relates to adenoviral vectors. More particularly, this invention relates to recombinant high capacity adenoviral vectors which can be employed in the treatment of hemophilia A.

BACKGROUND OF THE INVENTION

Hemophilia A is an X-linked, recessive bleeding disorder caused by deficiency of clotting Factor VIII ("FVII"). In the United States alone there are approximately 20,000 patients with hemophilia A. The clinical presentation for hemophilia A is characterized by episodes of spontaneous and prolonged bleeding. Currently, hemophilia A is treated with protein replacement therapy using either plasma-derived or recombinant FVIII. Although FVIII replacement markedly improved the life expectancy of patients suffering from hemophilia, they are still at risk for severe bleeding episodes and chronic joint damage, since prophylactic treatment is restricted by the short half-life, the limited availability and the high cost of purified FVIII, which can approach $100,000/patient/year. In addition, the use of plasma-derived factors obtained from contaminated blood sources increases the risk of viral transmission. Gene therapy offers the promise of a new method of treating hemophilia A, since the therapeutic window is relatively broad and levels slightly above 1% of normal physiological levels are therapeutic (see, Kay M A, High K. Gene therapy for the hemophilias [comment]. Proc Natl Acad Sci USA. 1999; 96:9973-9975). If successful, gene therapy could provide constant FVIII synthesis which may lead to a cure for this disease. Different viral and non-viral gene therapy methods have been evaluated for the treatment of patients suffering from hemophilia A (see, e.g., Chuah M K, Collen D, VandenDriessche T. Gene therapy for hemophilia: hopes and hurdles. Crit Rev Oncol Hematol. 1998; 28:153-171 and Chuah M K, Collen D, VandenDriessche T. Gene therapy for hemophilia. J Gene Med. 2001; 3:3-20). Adenoviral (Ad) vectors are the most efficient vectors for hepatic gene delivery (Ibid.). The adenoviral vector genome remains episomal, implying that the risk of neoplastic transformation due to insertional mutagenesis is low. However, early-generation adenoviral vectors still contain most viral genes. Their expression contributes to inflammatory responses, toxicity and short-term transgene expression (see, e.g. Yang Y, Su Q, Wilson J M. Role of viral antigens in destructive cellular immune responses to adenovirus vector-transduced cells in mouse lungs. J Virol. 1996, 70:7209-7212; Fang B, Wang H, Gordon G, Bellinger D A, Read M S, Brinkhous K M, Woo S L, Eisensmith R C. Lack of persistence of E1-recombinant adenoviral vectors containing a temperature-sensitive E2A mutation in immunocompetent mice and hemophilia B dogs. Gene Ther. 1996, 3:217-222; Schiedner G, Morral N, Parks R J, Wu Y, Koopmans S C, Langston C, Graham F L, Beaudet A L, Kochanek S. Genomic DNA transfer with a high-capacity adenovirus vector results in improved in vivo gene expression and decreased toxicity [published erratum appears in Nat Genet 1998 March; 18(3):298]. Nat Genet. 1998, 18:180-183; Yang Y, Ertl H C, Wilson J M. MHC class I-restricted cytotoxic T lymphocytes to viral antigens destroy hepatocytes in mice infected with E1-deleted recombinant adenoviruses. Immunity. 1994, 1:433-442; Yang Y, Li Q, Ertl H C, Wilson J M. Cellular and humoral immune responses to viral antigens create barriers to lung-directed gene therapy with recombinant adenoviruses. J Virol. 1995, 69:2004-2015; and Yang Y, Jooss K U, Su Q, Ertl H C, Wilson J M. Immune responses to viral antigens versus transgene product in the elimination of recombinant adenovirus-infected hepatocytes in vivo. Gene Ther. 1996; 3:137-144). Studies in the art have shown that injection of early-generation adenoviral vectors encoding canine or human FVIII resulted in efficient liver transduction and in therapeutic levels of FVIII in hemophilic mice, dogs or rhesus macaques (see, e.g., Connelly S, Smith T A, Dhir G, Gardner J M, Mehaffey M G, Zaret K S, McClelland A, Kaleko M. In vivo gene delivery and expression of physiological levels of functional human factor VIII in mice. Hum Gene Ther. 1995, 6:185-193; Connelly S, Gardner J M, McClelland A, Kaleko M. High-level tissue-specific expression of functional human factor VIII in mice. Hum Gene Ther. 1996, 7:183-195; Connelly S, Mount J, Mauser A, Gardner J M, Kaleko M, McClelland A, Lothrop C D, Jr. Complete short-term correction of canine hemophilia A by in vivo gene therapy. Blood. 1996, 88:3846-3853; Connelly S, Andrews J L, Gallo A M, Kayda D B, Qian J, Hoyer L, Kadan M J, Gorziglia M I, Trapnell B C, McClelland A, Kaleko M. Sustained phenotypic correction of murine hemophilia A by in vivo gene therapy. Blood. 1998, 91:3273-3281; and Gallo-Penn A M, Shirley P S, Andrews J L, Tinlin S, Webster S, Cameron C, Hough C, Notley C, Lillicrap D, Kaleko M, Connelly S. Systemic delivery of an adenoviral vector encoding canine factor VIII results in short-term phenotypic correction, inhibitor development, and biphasic liver toxicity in hemophilia A dogs. Blood. 2001; 97:107-113). However, FVIII levels declined to baseline, possibly due to vector toxicity related to residual adenoviral gene expression. In the dog model, induction of antibody immune responses against FVIII was associated with only transient correction of the bleeding diathesis (see, Gallo-Penn, et al. supra). Inflammatory responses and vector toxicity further diminished the therapeutic efficacy (Ibid.). To overcome the limitations of early-generation adenoviral vectors, novel adenoviral vectors have been developed, designated as high-capacity (HC), helper-dependent (HD) or "gutless" adenoviral vectors, which are devoid of all adenoviral genes. These HC-Ad vectors retain only the necessary cis-acting elements that are required for generating infectious vector particles during vector production and typically depends on the use of an E1-complementation cell line and a packaging-defective helper virus that provides the necessary viral functions in trans (see, Kochanek S. High-capacity adenoviral vectors for gene transfer and somatic gene therapy. Hum Gene Ther. 1999, 10:2451-2459 and Parks R J, Chen L, Anton M, Sankar U, Rudnicki M A, Graham F L. A helper-dependent adenovirus vector system: removal of helper virus by Cre-mediated excision of the viral packaging signal. Proc Natl Acad Sci USA. 1996, 93:13565-13570). However, notwithstanding the improvements of these HC-Ad vectors, the therapeutic application of said vectors still causes toxicity to the host. This toxicity is mainly due to the need for the use of a high amount of infectious units of recombinant vector and results in the activation of the innate immune system, in liver toxicity and may contribute to the induction of a humoral immune response. Thus, there is a need to apply lower vector doses to reduce undesirable side effects.

SUMMARY

In one embodiment of the present invention we have generated recombinant HC-Ad vectors comprising Factor VIII that produce unprecedented, high levels of human or canine Factor VIII (exceeding 1500% of physiologic Factor VIII levels). These recombinant vectors can be used in methods and processes which utilize much lower doses than described in the art to cure hemophilia A in a clinically relevant animal model. HC-Ad vectors expressing human or canine B-domain deleted FVIII genes from different liver-specific promoters were injected into FVIII-deficient mice that suffered from hemophilia A. Furthermore, in immunodeficient FVIII-deficient mice hepatic gene transfer resulted in long-term expression of human or canine FVIII at supraphysiologic levels correcting the bleeding disorder. Serum transaminase levels and cytokine profiles confirmed the safety of this recombinant of adenoviral vectors.

BRIEF DESCRIPTION OF THE SEVERAL VIEWS OF THE DRAWINGS

FIG. 1A and FIG. 1B illustrate the design of HC-Ad vectors. The Ad-AAT-cFVIII and Ad-AAT-hFVIII vectors carry the human alfa1-antitrypsin promoter (AAT) to direct the expression of the canine or human B-domain deleted FVIII cDNA, respectively (FIG. 1A). An HPRT stuffer fragment was employed to optimize vector size and to avoid vector rearrangements. In the Ad-Apo-cFVIII vector, the B-domain deleted FVIII cDNA. was expressed from the hepatocyte-specific chimeric ApoE/ApoCII promoter (Apo) (FIG. 1B). An additional stuffer sequence derived from the C346 cosmid fragment was used in the Ad-Apo-cFVIII vector.

FIG. 7 depicts a toxicity analysis of HC-Ad vectors. AST (black bars) and ALT (grey bars) levels (A), platelet counts (B) and IL-6 levels (C) in plasma from FVIIIKO-SCID mice intravenously injected with $5 \times 10^9$ i.u. of Ad-AAT-cFVIII, Ad-AAT-hFVIII and Ad-Apo-cFVIII.

DETAILED DESCRIPTION OF THE INVENTION

Figure 1A:
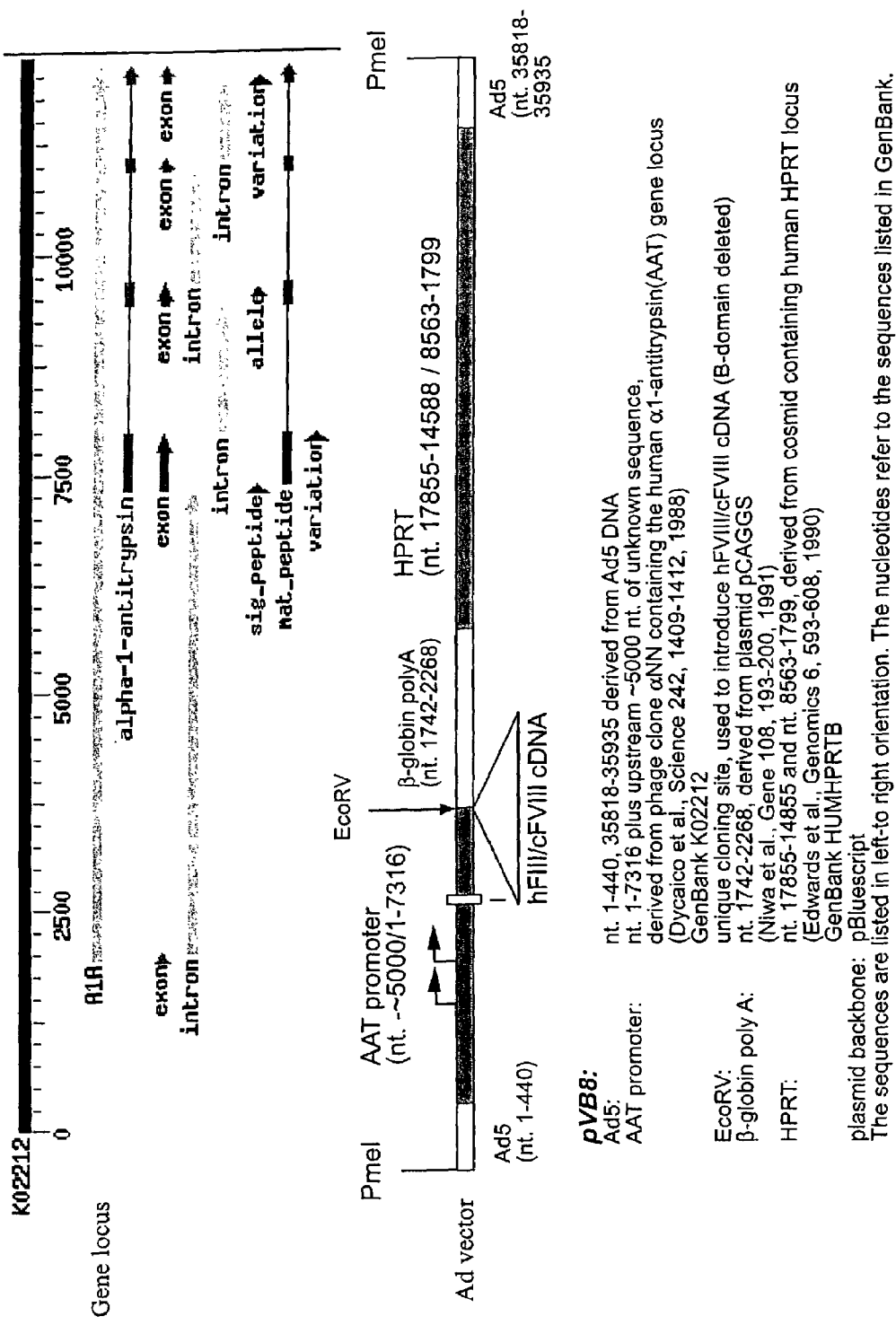

The current invention shows that unprecedented, high levels of human or canine B-domain deleted factor VIII are produced in adult hemophilic mice following gene therapy with the recombinant HC-Ad vectors of the invention. Using a vector dose of $5 \times 10^9$ i.u. in FVIII-deficient SCID mice stable FVIII expression levels exceeding 15,000 mU/ml were observed. This is at least 15-fold higher than the physiologic levels of FVIII in plasma of humans. Even at the 50-fold lower vector dose of $10^8$ i.u., physiologic FVIII levels were still observed, contrary to previous studies in which FVIII expression was undetectable with comparable vector doses (see, e.g., Balague C, Zhou J, Dai Y, Alemany R, Josephs S F, Andreason G, Hariharan M, Sethi E, Prokopenko E, Jan H Y, Lou Y C, Hubert-Leslie D, Ruiz L, Zhang W W. Sustained high-level expression of full-length human factor VIII and restoration of clotting activity in hemophilic mice using a minimal adenovirus vector. Blood. 2000, 95:820-828). In immunocompetent FVIII-deficient mice, human or canine FVIII expression was also very high, with peak levels between 40,000 and 75,000 mU/ml corresponding to levels 40 to 75-fold above the normal physiologic FVIII levels. Hence, the use of HC-Ad vectors resulted in FVIII levels that were 1,000 to 10,000-fold higher than the therapeutic threshold concentration of 1% that is needed to convert severe to moderate hemophilia. Most importantly, injection of a relatively low vector dose ($10^8$ infectious units) still resulted in physiologic FVIII levels, whereas in previous studies no FVIII levels could be detected at these low vector doses using a high-capacity adenoviral vector that is currently in clinical trials (Balague et al. (2000) Blood 95:820). Following transient in vivo depletion of macrophages prior to gene transfer, significantly higher and stable FVIII expression levels were observed. Strikingly, the injection of only $5 \times 10^6$ HC-Ad vectors after macrophage depletion resulted in long-term therapeutic FVIII levels in the FVIIIKO and FVIIIKO-SCID mice. Vector doses that were 1000-fold higher than this lowest therapeutic dose triggered no or only transient elevations in serum transaminases. Vector administration did not result in thrombocytopenia, anemia or elevation of pro-inflammatory cytokines (IL-6). The invention further shows that the recombinant HC-Ad vectors are suited for preclinical trials in hemophilia A dogs in anticipation of clinical trials in patients suffering from hemophilia A.

In accordance with an aspect of the present invention, there is provided a high capacity recombinant adenoviral vector including at least one DNA sequence encoding a Factor VIII clotting factor. The term "DNA sequence encoding a Factor VIII clotting factor" as used herein means DNA which encodes a full-length clotting factor or a fragment, a B-domain deleted Factor VIII, a derivative, or analogue of a Factor VIII clotting factor, i.e., such DNA may be a full-length gene encoding a full-length Factor VIII clotting factor, or a truncated gene, or a mutated gene encoding a fragment, B-domain deleted or derivative or analogue of such Factor VIII clotting factor which has Factor VIII clotting factor activity. The term "DNA sequence" refers generally to a polydeoxyribonucleotide molecule and more specifically to a linear series of deoxyribonucleotides connected one to the other by phosphodiester bonds between the 3' and 5' carbons of the adjacent pentoses. DNA sequences encoding Factor VIII and fragments or derivatives thereof are shown and described in U.S. Pat. No. 4,757,006 issued Jul. 12, 1988 to Toole, Jr. et al.; U.S. Pat. No. 4,868,112 issued Sep. 19, 1989 to Toole, Jr.; U.S. Pat. No. 5,045,455 issued Sep. 3, 1991 to Kuo et al; U.S. Pat. No. 5,004,804 issued Apr. 2, 1991 to Kuo et al.; U.S. Pat. No. 5,112,950 issued May 12, 1992 to Meulien et al.; and U.S. Pat. No. 5,149,637 issued Sep. 22, 1992 to Scandella et al. The inventors have found that, by infecting host cells in vivo with high capacity adenoviral vectors including at least one DNA sequence encoding a Factor VIII clotting factor, one is able to achieve expression, in vivo, of the clotting factor, or fragment, B-domain deleted or derivative or analogue of such Factor VIII clotting factor having Factor VIII clotting factor activity, at effective therapeutic levels.

The DNA sequence encoding a Factor VIII clotting factor is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus promoter; the Rous Sarcoma Virus (RSV) promoter; the albumin promoter; inducible promoters, such as the Mouse Mammary Tumor Virus (MMTV) promoter; the metallothionein promoter; heat shock promoters; the .alpha.-1-antitrypsin promoter; the hepatitis B surface antigen promoter; the transferrin promoter; the apolipoprotein A-1 promoter; the Factor VIII promoter. It is to be understood, however, that the scope of the present invention is not to be limited to specific promoters.

In a particular embodiment, when the DNA sequence encodes Factor VIII or a fragment, B-domain deleted, derivative, or analogue thereof, the promoter controlling the DNA sequence is preferably a tissue-specific promoter, such as, for example, the human alfa1-antitrypsin promoter (AAT). In another embodiment the promoter is the human hepatocyte-specific chimeric ApoE/ApocII promoter (Apo) (deposited on Sep. 2, 2004, under Accession number LMBP 4934 at the Belgian Coordinated Collections of Microorganisms-BCCM™, Laboratorium voor Moleculaire Biologies-Plasmidencollectie (LMBP), Universiteit Gent, Technologiepark 927, B-9052 Gent-Zwijnaarde, Belgium).

In another embodiment, the DNA sequence encoding a FVIII clotting factor also may include introns and other genomic elements to enhance expression. The term "genomic element," as used herein, means a sequence of nucleotides in a naturally occurring gene that is not normally incorporated into the cDNA, and which is not part of the adenoviral genome. Such genomic elements which may be included in the vector include, but are not limited to, introns, the 5' untranslated region, and the 3' untranslated region of the gene encoding the clotting factor, or portions of such 5' and 3' untranslated regions and introns. Examples of introns which may be employed include, but are not limited to any of the twenty-five introns of the Factor VIII gene (Gitschier, Nature, 312:326-330 (1984)), or portions thereof; or the first exon and intron of the apolipoprotein A-1 gene.

In a particular embodiment, the recombinant adenoviral vector comprises the Ad5 left terminus, a promoter, a Factor VIII cDNA wherein the B-domain has been deleted and the Ad5 right terminus. In another particular embodiment said FVIII cDNA is human FVIII cDNA. In another particular embodiment said FVIII cDNA is canine FVIII cDNA.

In another embodiment the recombinant high capacity adenoviral vectors of the current invention can be used for the manufacture of a medicament to treat haemophilia A.

The recombinant high capacity adenoviral vector, consisting of infectious which comprise at least one DNA sequence encoding a Factor VIII clotting factor, is administered in an amount effective to treat hemophilia A in a host. In one embodiment, the vector particles may be administered in an amount of less than $10^{10}$ infectious units per kg of a recombinant adenoviral vector. In yet another embodiment, the vector particles may be administered in an amount of less than $10^{10}$ infectious units per kg of the recombinant high capacity adenoviral vectors from the present invention. In yet another embodiment the vector particles may be administered in an amount of less than $8.10^9$, $6.10^9$, $4.10^9$, $2.10^9$, $10^9$ or even less amounts of infectious units per kg of the recombinant high capacity adenoviral vectors from the present invention. The amount of infectious units of a sample comprising a recombinant adenoviral vector can be measured according to various methods described in the art. For example the determination of infectious units is based on DNA slot blot titers following in vitro transduction of cells with the HC-Ad vector as described previously (Kreppel et al., a DNA based method to assay total and infectious particle contents and helper virus contamination in high-capacity adenoviral vector preparations is described in. Hum. Gene Ther., 13 (10), 2002). For the extrapolation of calculations per kilogram we assumed that a mouse weighs about 30 grams.

In yet another embodiment, the vector particles may be administered in an amount of less than $10^{12}$ viral particles per kg of a recombinant adenoviral vector. In yet another embodiment the vector particles may be administered in an amount of less than $10^{12}$ viral particles per kg of the recombinant high capacity adenoviral vectors from the present invention. In yet another embodiment the vector particles may be administered in an amount of less than $8.10^{11}$, $6.10^{11}$, $4.10^{11}$, $2.10^{11}$, $10^{11}$ or even less amounts of viral particles per kg of the recombinant high capacity adenoviral vectors from the present invention. The amount of viral particles of a recombinant adenoviral vector can for example be measured by measuring the optical density of a solution of viral particles at a wavelength of 280 nanometer.

The host may be a human or non-human animal host. The preferred non-human animal host is a mammal, most preferably a dog or a non-human primate. Preferably, the infectious vector particles are administered systemically, such as, for example, by intravenous administration (such as, for example, via peripheral vein injection) or administered via the portal vein, to the bile duct, intramuscularly, intraperitoneally, or intranasally. The vector particles may be administered in combination with a pharmaceutically acceptable carrier suitable for administration to a patient. The carrier may be a liquid carrier (for example, a saline solution), or a solid carrier, such as, for example, mirocarrier beads.

The current invention is in accordance with the Orkin-Motulsky report which assessed the status and promise of gene therapy and provided recommendations regarding future research in this area. The invention will now be described with respect to the following examples; however, the scope of the present invention is not to be limited thereby.

EXPERIMENTAL SECTION

EXAMPLE 1

Generation of HC-Ad Vectors

Three different HC-Ad vectors were compared in the present study (FIG. 1). The Ad-AAT-cFVIII and Ad-AAT-hFVIII vectors express the canine or human B-domain deleted FVIII cDNA, respectively, from the human alfa1-antitrypsin promoter (AAT) (FIGS. 1A & B). An HPRT stuffer fragment was employed to optimize vector size and to avoid vector rearrangements (Parks R J, Graham F L. A helper-dependent system for adenovirus vector production helps define a lower limit for efficient DNA packaging. J Virol. 1997, 71:3293-3298). The rationale for using the AAT promoter was based on previous studies indicating that this promoter can lead to long-term, liver-specific expression of therapeutic proteins following transduction with HC-Ad vectors into immunocompetent mice and baboons (see, Schiedner G, Morral N, Parks R J, Wu Y, Koopmans S C, Langston C, Graham F L, Beaudet A L, Kochanek S. Genomic DNA transfer with a high-capacity adenovirus vector results in improved in vivo gene expression and decreased toxicity [published erratum appears in Nat Genet 1998 March; 18(3):298]. Nat Genet. 1998, 18:180-183; Morral N, O'Neal W, Rice K, Leland M, Kaplan J, Piedra P A, Zhou H, Parks R J, Velji R, Aguilar-Cordova E, Wadsworth S, Graham F L, Kochanek S, Carey K D, Beaudet A L. Administration of helper-dependent adenoviral vectors and sequential delivery of different vector serotype for long-term liver-directed gene transfer in baboons. Proc Natl Acad Sci USA. 1999, 96:12816-12821; and Schiedner G, Hertel S, Johnston M, Biermann V, Dries V, Kochanek S. Variables affecting in vivo performance of high-capacity adenovirus vectors. J Virol. 2002; 76:1600-1609). In an alternative vector design (Ad-Apo-cFVIII) the canine B-domain deleted FVIII cDNA was under control of the hepatocyte-specific chimeric ApoE/ApoCII promoter (Apo). In this vector an additional fragment from the C346 cosmid was included. The average particle titers obtained with the Cre66 packaging cell line were comparable for the different vectors: $9.2 \times 10^{11}$ particles/ml for Ad-AAT-cFVIII, $9.3 \times 10^{11}$ particles/ml for Ad-AAT-hFVIII, and $8.4 \times 10^{11}$ particles/ml for Ad-Apo-cFVIII. The average infectious titers as determined by slot blot analyses (Kreppel et al., submitted) were $2.8 \times 10^{10}$ infectious units/ml for Ad-AAT-cFVIII, $2.7 \times 10^{10}$ infectious units/ml for Ad-AAT-hFVIII, and $1 \times 10^{10}$ infectious units/ml for Ad-Apo-cFVIII. DNAs from CsCl-purified vectors were analyzed by restriction digestion and did not show any rearrangements.

EXAMPLE 2

HC-Ad Mediated FVIII Gene Delivery in Immunodeficient Hemophilic Mice

Figure 2:
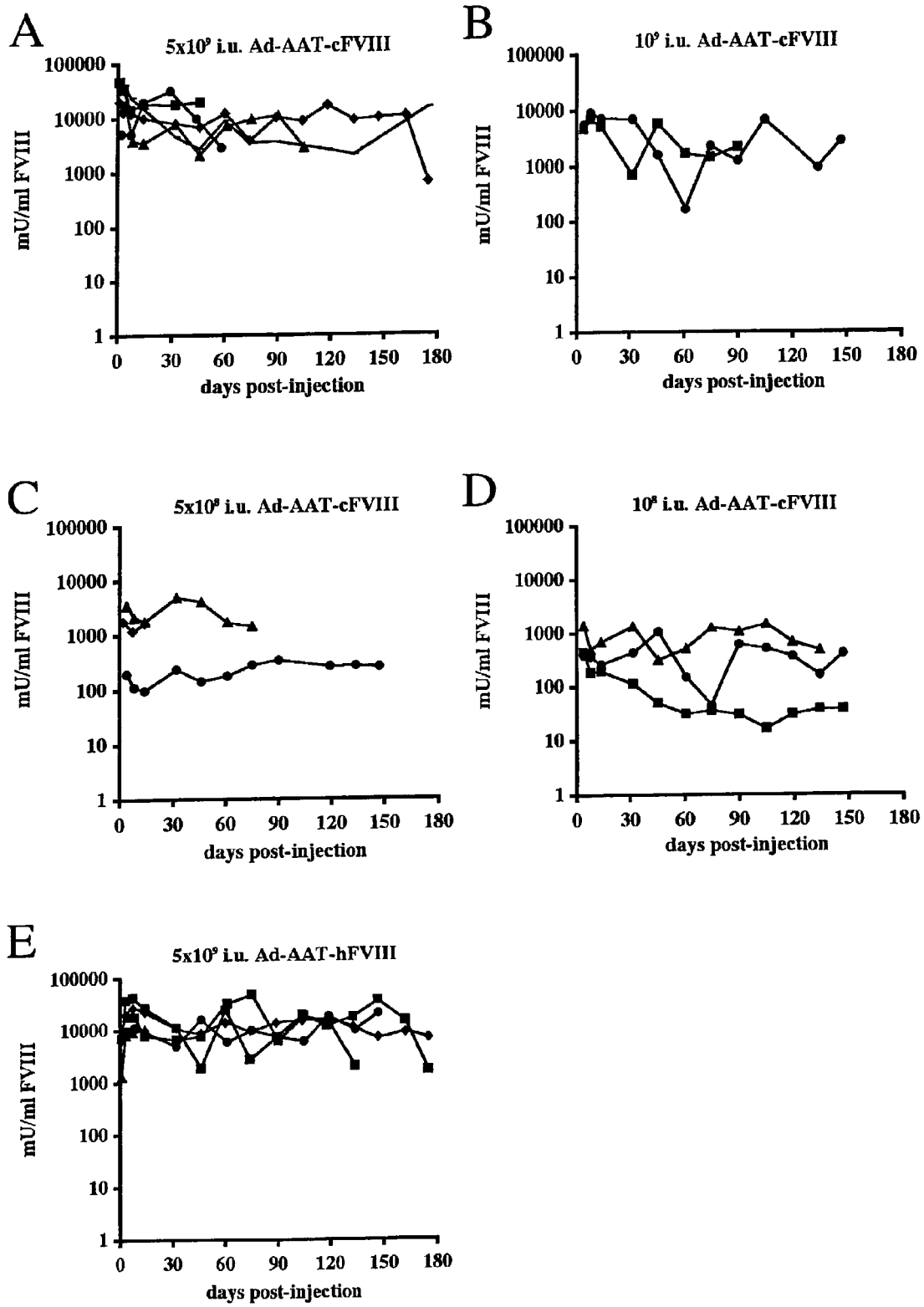
FIG. 2 depicts functional FVIII expression kinetics in adult hemophilic FVIIIKO-SCID mice following HC-Ad gene transfer. Mice were injected intravenously with the Ad-AAT-cFVIII at a dose of $5 \times 10^9$ (A), $10^9$ (B) $5 \times 10^8$ (C) and $10^8$ i.u. (D) or with Ad-AAT-hFVIII at a dose of $5 \times 10^9$ i.u. (E). FVIII-deficient littermates were injected with PBS as control.

Adult hemophilic FVIIIKO-SCID mice were intravenously injected with the Ad-AAT-cFVIII vector at doses of $5 \times 10^9$, $10^9$, $5 \times 10^8$ and $10^8$ i.u. (FIG. 2A-D). FVIII-deficient littermates were injected with PBS as control. Immunodeficient hemophilic mice were chosen to assess the long-term expression potential of these non-integrating vector type in the absence of confounding immune responses against the human or canine FVIII xenoproteins. The FVIII production in the plasma of recipient mice was determined using a functional FVIII chromogenic assay. The FVIII expression levels were dose dependent with the three highest doses showing supraphysiologic FVIII levels (>1000 mU/ml) (FIG. 2). At the highest vector dose ($5 \times 10^9$ i.u.) supraphysiologic canine FVIII levels were achieved for at least 6 months, stabilizing above the 15,000 mU/ml level (FIG. 2A). These levels are at least 15-fold higher than the FVIII concentration in normal human plasma. Peak FVIII production levels corresponding to nearly 50,000 mU/ml were observed. Even at the lowest vector dose ($10^8$ i.u.), physiologic FVIII concentrations were still observed in most recipient mice (i.e. 1000 mU/ml). Control animals injected with PBS had no detectable FVIII activity (<25 mU/ml=background level).

In parallel, adult hemophilic FVIIIKO-SCID mice were intravenously injected with $5 \times 10^9$ i.u. of Ad-AAT-hFVIII (n=5) (FIG. 2E). Supraphysiologic human FVIII levels (exceeding 15,000 mU/ml) were obtained for at least 6 months, consistent with the results obtained with the Ad-AAT-cFVIII vector. Similarly, long-term expression of supraphysiologic human or canine FVIII levels were achieved in NOD-SCID mice.

To further assess phenotypic correction of the clotting deficiency, plasma samples were subjected to a functional clotting assay (aPTT) that measures the activated partial thromboplastin time. The clotting time was significantly reduced (t-test: P<0.001) in plasma obtained from hemophilic FVIIIKO-SCID mice that were injected with $5 \times 10^9$ i.u. Ad-AAT-cFVIII (22±8 s) and Ad-AAT-hFVIII vectors (40±7 s) compared to the clotting time of plasma from untreated hemophilic FVIIIKO-SCID mice (90±10 s) (n=3). The clotting time of plasma from hemophilic animals injected with the FVIII vectors was similar or even lower than of plasma from non-hemophilic mice (40±4 sec). Hence, gene therapy using HC-Ad vectors stably corrected the bleeding diathesis of these hemophilic mice.

EXAMPLE 3

HC-Ad Mediated FVIII Gene Delivery in Immunocompetent Hemophilic Mice

Figure 3:
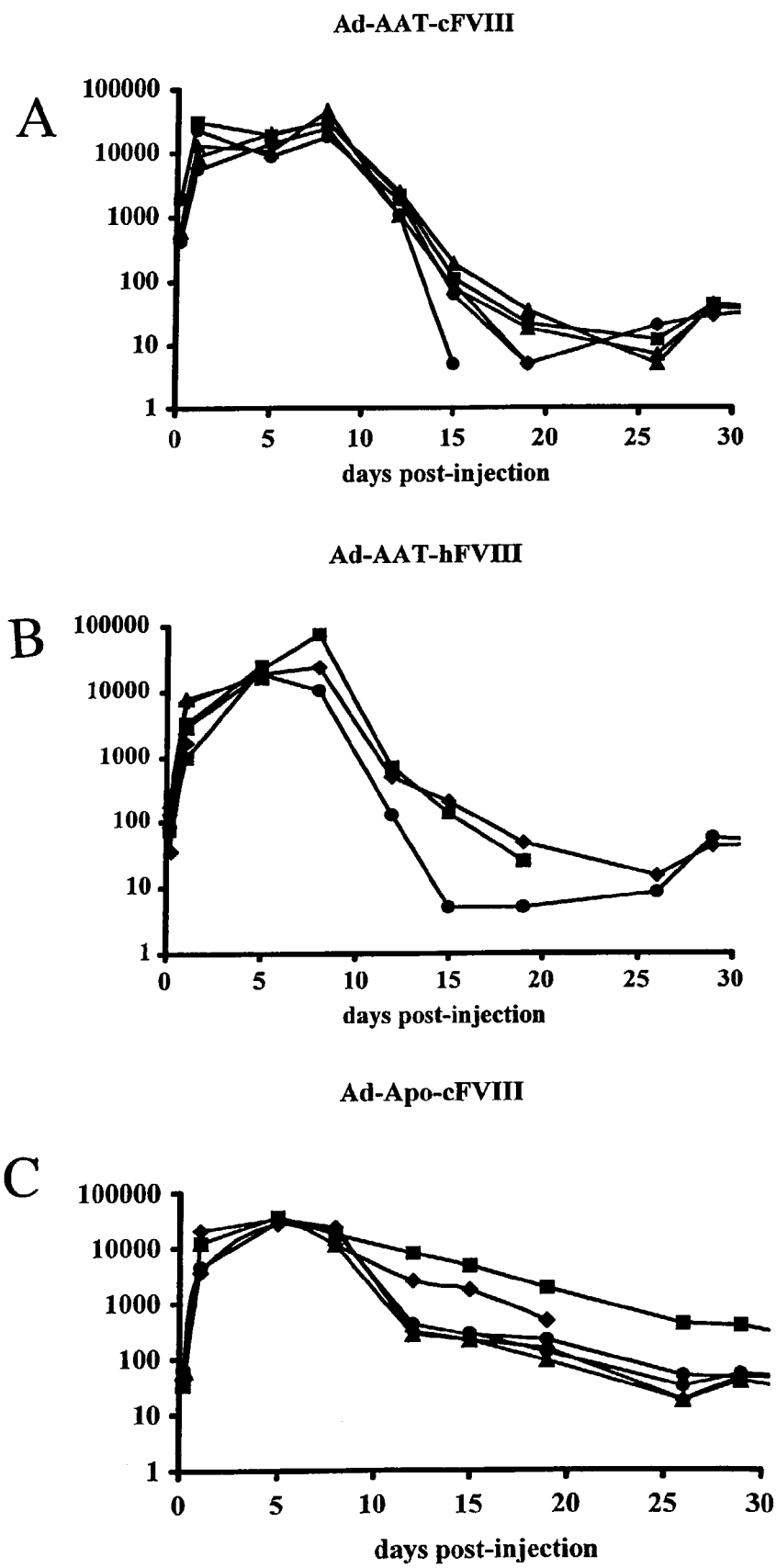
FIG. 3 depicts functional FVIII expression kinetics in adult hemophilic FVIIIKO mice following HC-Ad gene transfer. Mice were injected intravenously with Ad-AAT-cFVIII (A), Ad-AAT-hFVIII (B) and Ad-Apo-cFVIII (C) at $5 \times 10^9$ i.u. per mouse (n=6 for each vector).

To evaluate FVIII expression kinetics in immunocompetent animals, adult hemophilic FVIIIKO mice were intravenously injected with Ad-AAT-cFVIII and Ad-AAT-hFVIII at a dose of $5 \times 10^9$ i.u. (n=6 for each vector). FVIII peak expression levels were observed within 5 to 8 days post-injection (FIGS. 3A & 3B). These peak levels corresponded to 50,000 mU/ml for Ad-AAT-cFVIII and 75,000 mU/ml for Ad-AAT-hFVIII. FVIII levels had fallen to baseline 3-4 weeks post-injection. This decrease in FVIII expression coincided with the induction of high-titer neutralizing antibodies (clinically referred to as "inhibitors") directed against the xenogeneic FVIII protein (55±45 Bethesda Units/ml).

EXAMPLE 4

Comparison of ApoE/ApoCII Hepatocyte-specific Promoter with AAT Promoter

Previous studies had suggested that inadvertent expression of transgenes in antigen-presenting cells might lead to the formation of neutralizing antibodies against the transgene product (see, Pastore L, Morral N, Zhou H, Garcia R, Parks R J, Kochanek S, Graham F L, Lee B, Beaudet A L. Use of a liver-specific promoter reduces immune response to the transgene in adenoviral vectors. Hum Gene Ther. 1999, 10:1773-178). Since the AAT promoter is likely active in macrophage-like cells, possibly including Kupffer cells (Schiedner et al. 1998, supra), it was important to rule out that the formation of neutralizing antibodies is due to the use of the AAT promoter that controls FVIII expression. An alternative HC-Ad was therefore evaluated which drives the canine B-domain deleted FVIII gene from a chimeric ApoE/ApoCII hepatocyte-specific promoter (Ad-Apo-cFVIII). Intravenous injection of FVIIIKO mice with $5 \times 10^9$ i.u. of Ad-Apo-cFVIII lead to supraphysiologic FVIII plasma concentration (up to 40,000 mU/ml) about 5 to 8 days post-injection (FIG. 3C). Thereafter and within 3 to 4 weeks post-injection expression declined to basal levels, which ressembled the FVIII expression kinetics of the Ad-AAT-cFVIII and Ad-AAT-hFVIII vectors. This decline correlated with the induction of neutralizing antibodies against canine FVIII (160±150 Bethesda Units/ml). Thus, the decline in human or canine FVIII expression in FVIIIKO mice was not inherent to the use of the AAT promoter. Following injection of Ad-Apo-cFVIII into FVIIIKO-SCID (FIG. 2) and NOD-SCID mice, continuous FVIII expression (>3 months) in the supraphysiologic range (exceeding 15,000 mU/ml) was observed, consistent with the expression profiles of Ad-AAT-cFVIII and Ad-AAT-hFVIII. Gene therapy using the Ad-Apo-cFVIII vector stably corrected the bleeding diathesis of these hemophilic mice. The clotting time based on aPTT assays was significantly reduced (t-test: P<0.001) in plasma obtained from hemophilic FVIIIKO-SCID mice that were injected with $5 \times 10^9$ i.u. Ad-Apo-cFVIII (27±5 s) compared to that of plasma from untreated hemophilic FVIIIKO-SCID mice (90±10 s) (n=3).

EXAMPLE 5

Figure 4:
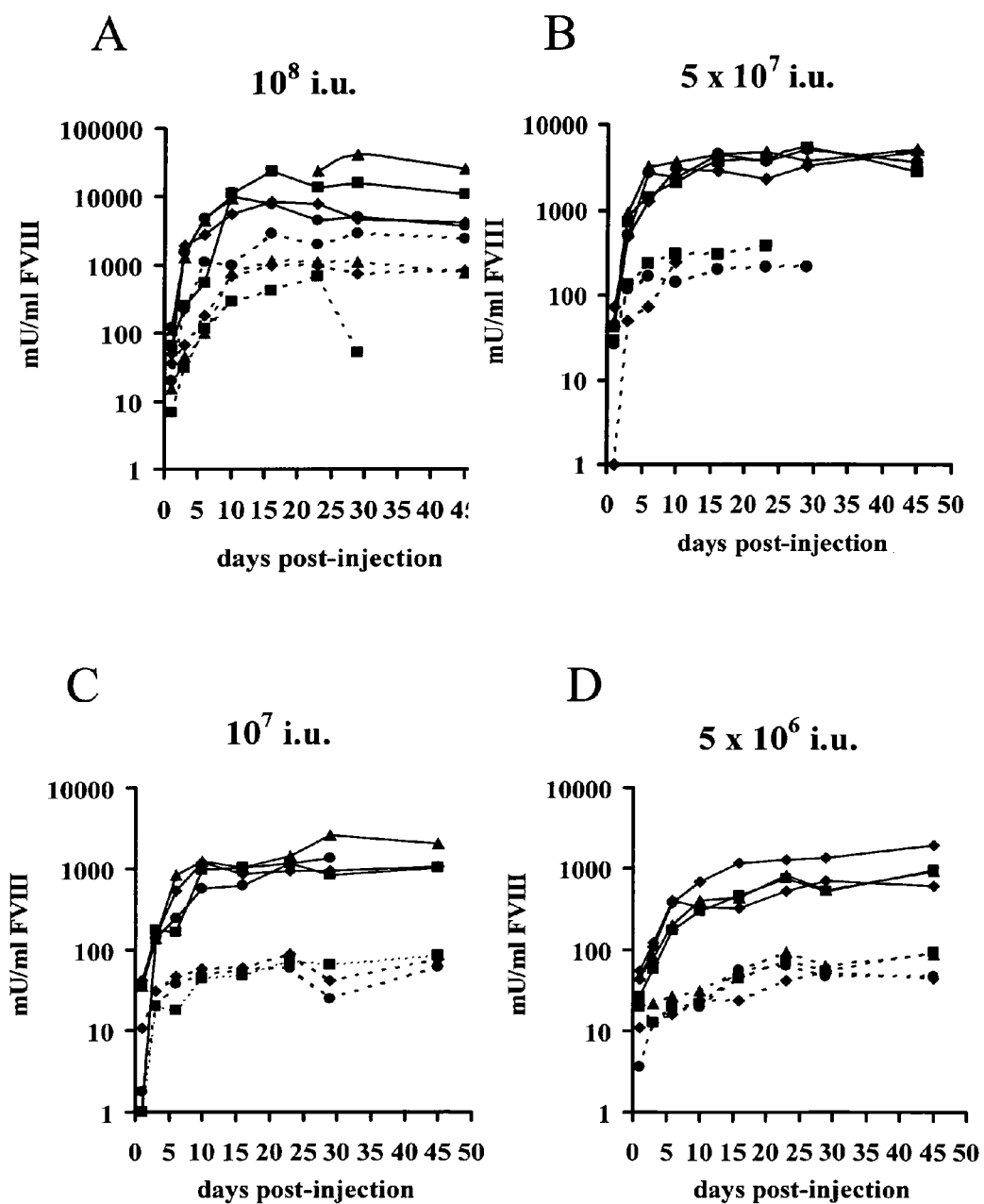
FIG. 4 depicts functional FVIII expression in FVIIIKO-SCID mice following transient macrophage depletion. Experimental mice were injected with clodronate liposomes (black lines) one day prior to the injection with Ad-AAT-cFVIII at different doses: $10^8$ (A), $5 \times 10^7$ (B), $10^7$ (C) and $5 \times 10^6$ i.u. (D). Littermates were injected with PBS-containing liposomes as controls (dashed lines).
Figure 5:
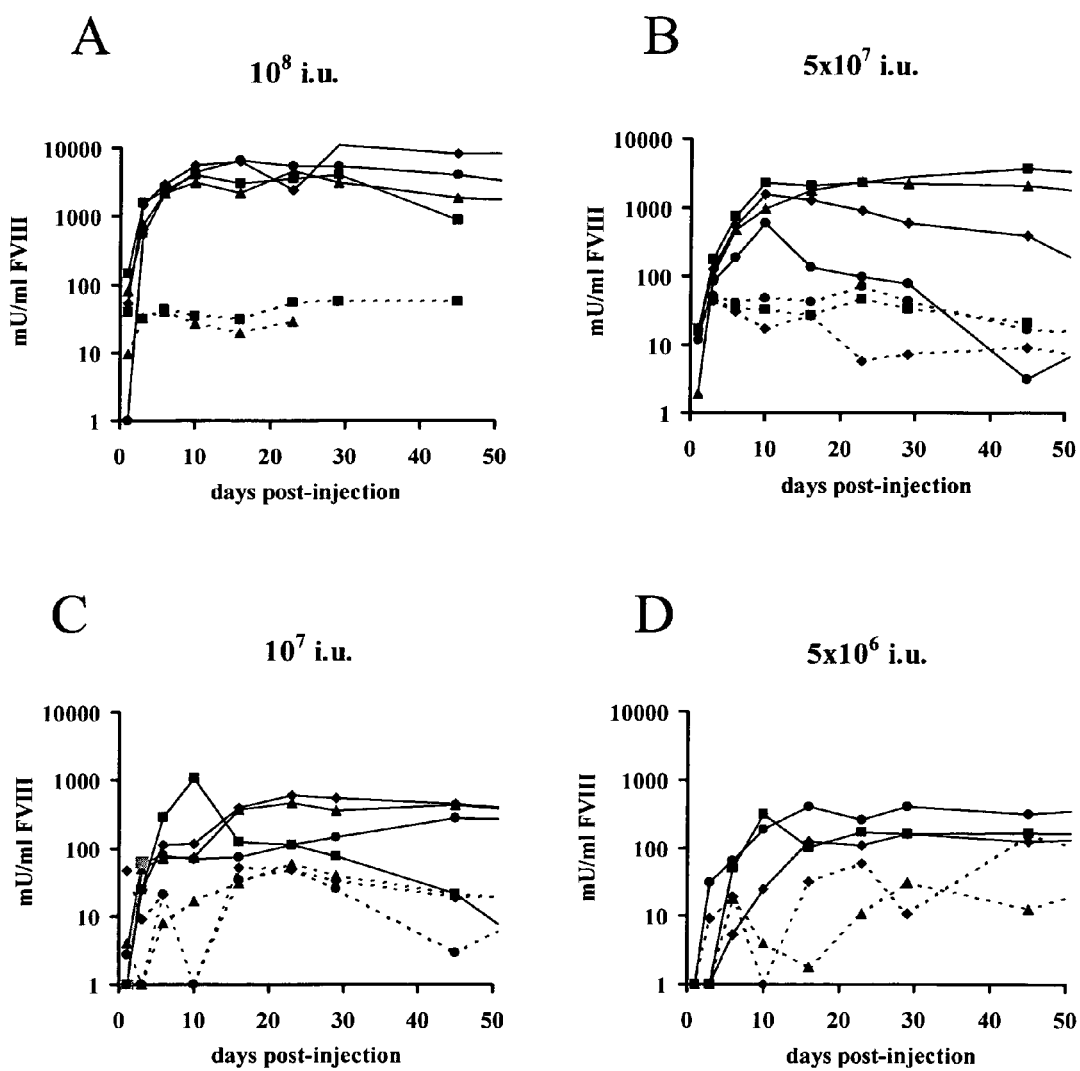
FIG. 5 depicts functional FVIII expression in FVIIIKO mice following transient macrophage depletion. Mice were treated with clodronate-liposomes (black lines) one day prior to injection of Ad-AAT-cFVIII vectors at different doses: $10^8$ (A), $5 \times 10^7$ (B), $10^7$ (C) and $5 \times 10^6$ i.u. (D). Littermates were injected with PBS-containing liposomes as controls. Littermates were injected with PBS-containing liposomes as controls (dashed lines).

Effect of Transient Macrophage Depletion on FVIII Expression in FVIIIKO and FVIIIKO-SCID Mice Transduced with HC-Ad Vectors The influence of cells of the innate immune system with regard to gene transfer efficiency using HC-Ad vectors has not been investigated. Therefore, the effect of transient depletion of tissue macrophages by injection of clodronate liposome injection on FVIII expression was evaluated in FVIIIKO and FVIIIKO-SCID mice. Littermates were injected with PBS-containing liposomes as controls. Injection of liposomes containing clodronate resulted in a significant decrease in liver and spleen macrophages compared to controls as confirmed by cytofluorimetric analysis using macrophage-specific markers (MHC class II and F4/80) (data not shown). One day after liposome injection FVIIIKO-SCID and FVIIIKO mice were injected with Ad-AAT-cFVIII at doses of $10^8$, $5 \times 10^7$, $10^7$ and $5 \times 10^6$ i.u. (FIGS. 4 & 5). In FVIIIKO-SCID mice, treatment with clodronate liposomes resulted in a 10-fold increase of FVIII expression (FIG. 4). Consequently, physiologic FVIII levels (1000 mU/ml) could still be achieved in the FVIIIKO-SCID mice using the lowest vector dose ($5 \times 10^6$ i.u.) whereas FVIII production was near background levels in FVIIIKO-SCID mice injected with PBS-liposomes (FIGS. 4C & D). FVIII expression was stable in FVIIIKO-SCID mice treated with either clodronate or PBS-liposomes, consistent with the results presented in FIG. 2.

In clodronate liposomes-treated FVIIIKO animals, dose-dependent and significantly increased FVIII expression levels were observed following Ad-AAT-cFVIII injection (FIG. 5). This is consistent with the results obtained in FVIIIKO-SCID mice (FIG. 4). Whereas supraphysiologic FVIII levels (exceeding 10,000 mU/ml) were achieved following administration of $10^8$ i.u. of Ad-AAT-cFVIII in clodronate liposomes-treated FVIIIKO mice, FVIII expression was near background levels (<25 mU/ml) in PBS-liposomes-treated controls. Even at the lowest Ad-AAT-cFVIII vector dose ($5 \times 10^6$ i.u.), therapeutic FVIII concentrations (i.e. exceeding 100 mU/ml) could still be obtained in most recipient FVIIIKO mice that had received clodronate liposomes (FIG. 5D). Most strikingly, clodronate liposome treatment resulted in relatively stable FVIII expression levels (>6 weeks) in most FVIIIKO mice that were injected with different doses of Ad-AAT-cFVIII. This was in contrast with the only short-term FVIII expression following Ad-AAT-cFVIII gene transfer in non-treated FVIIIKO mice (FIG. 3) secondary to antibody induction. Hence, a dual effect of clodronate liposome treatment was apparent in FVIIIKO mice: not only increased FVIII production, but also a significantly prolonged FVIII gene expression was observed.

EXAMPLE 6

Figure 6:
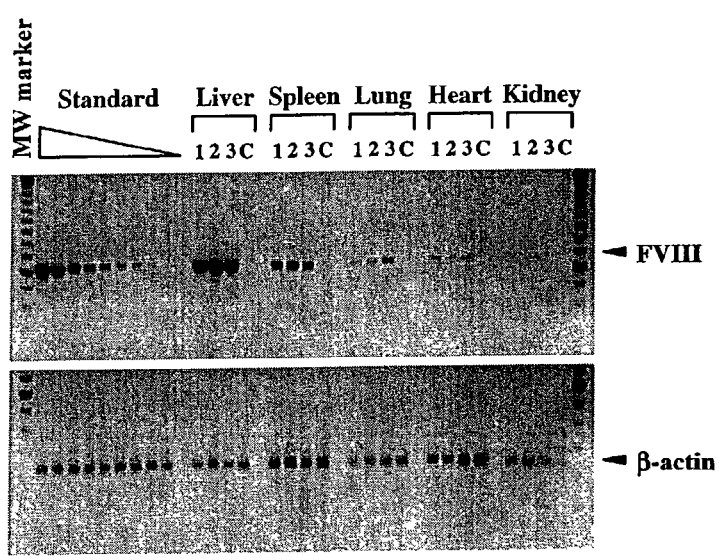
FIG. 6 depicts biodistribution of HC-Ad vectors, gene transfer efficiency and FVIII mRNA expression analysis. FVIIIKO mice were injected with $5 \times 10^9$ i.u. of Ad-AAT-hFVIII. Semi-quantitative PCR (A&B) or RT-PCR (C) using human FVIII-specific and alfa-actin specific primers (n=3 mice) at an early time-point (5 days post-injection: T1) (liver, spleen, lung, heart, kidney (A) and testis, gut and brain (B)). PCR analysis of liver and spleen at a late time-point (1 month post-injection: T2) is shown in (B). Mice injected with PBS were used as controls (lanes C). For RT-PCR analysis controls included samples without reverse transcriptase (No RT) to exclude genomic DNA contamination. Molecular weight (MW) marker was the 100 bp ladder. FVIII PCR generated a 0.6 kb fragment, alfa-actin PCR generated a 0.2 kb fragment. Standard corresponds to two-fold serially diluted DNA with known number of FVIII copies (ranging from 4 to 0 FVIII gene copies per diploid genomic equivalent).
Figure 6:
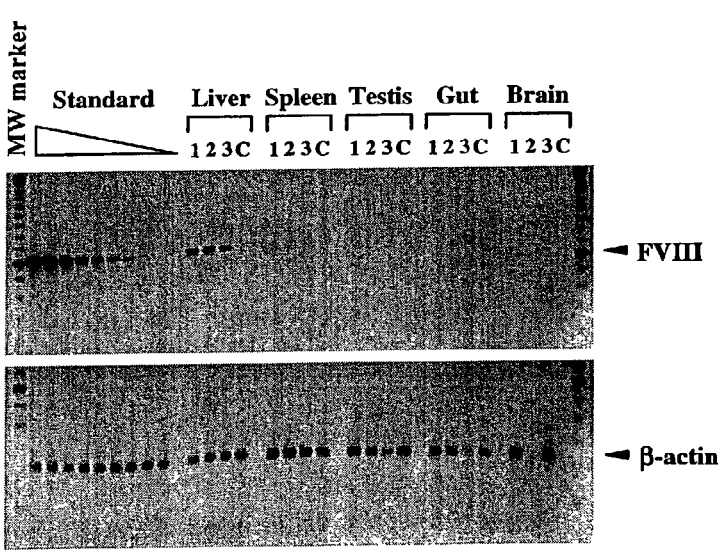
Figure 6:
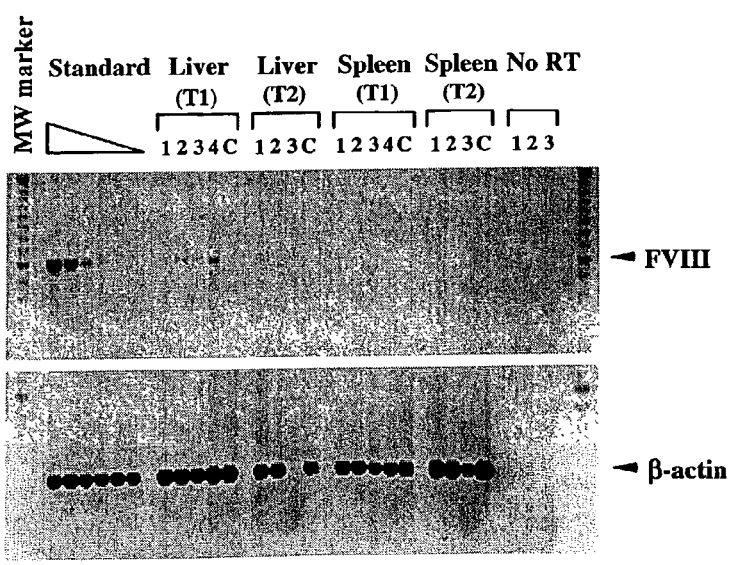

Biodistribution, Transduction Efficiency and Specificity of FVIII Expression Following HC-Ad Mediated FVIII Vector Administration Biodistribution and gene transfer efficiency of HC-Ad vectors was determined in FVIIIKO mice that were injected with $5 \times 10^9$ i.u. of Ad-AAT-hFVIII. Semi-quantitative PCR using human FVIII-specific primers indicated that gene transfer occurred predominantly into liver, spleen, lungs and heart. Vector-specific PCR fragments were not detected in testis, gut, brain or kidney (FIGS. 6A & B). The lack of detectable transgene-specific signals in the gonads suggested that the risk of inadvertent germline gene transfer following systemic administration of HC-Ad vectors may be relatively low. Nevertheless, additional experiments and more sensitive detection methods are required for a more in depth risk assessment. Gene transfer was more efficient in the liver than in any other organ. In addition, gene transfer in the spleen was more efficient than in heart and lungs (n=3). Five days post-injection, there were more transduced cells present in liver and spleen of recipient FVIIIKO mice than at a later time point (1 month post-injection, FIGS. 6A & B). As expected, human FVIII gene-specific bands were not detectable in control animals that were injected with PBS. To evaluate which transduced tissue expressed FVIII mRNA, semi-quantitative RT-PCR analysis was performed using human FVIII-specific primers. Human FVIII mRNA expression was detected in the liver but not in the other transduced organs, including spleen (FIG. 6C), lung or heart (data not shown). The apparent decrease of gene-marked cells in the liver (FIGS. 6A & B) correlated with a concomitant loss of hepatic human FVIII mRNA (FIG. 6C). As expected, endogenous alfa-actin mRNA could be detected by RT-PCR in spleen and liver (FIG. 6C), lungs and heart tissue (data not shown) of experimental (FIG. 6C) and negative control animals. The FVIII-specific RT-PCR product was not due to contaminating residual genomic DNA since controls without RT were negative (FIG. 6C).

EXAMPLE 7

Safety Assessment of HC-Ad Vectors

To evaluate potential hepatotoxicity associated with the use of HC-Ad vectors, liver transaminase levels (AST, ALT) (see, Lozier J N, Metzger M E, Donahue R E, Morgan R A.

Adenovirus-mediated expression of human coagulation factor IX in the rhesus macaque is associated with dose-limiting toxicity [see comments]. Blood. 1999, 94:3968-3975) were determined in the plasma at different intervals following injection of FVIIIKO-SCID mice with the highest dose of. $5 \times 10^9$ i.u. of the Ad-AAT-cFVIII, Ad-AAT-hFVIII and Ad-Apo-cFVIII vectors (FIG. 7A). The Ad-AAT-hFVIII and Ad-Apo-cFVIII vector preparations did not lead to a significant increase (P>0.05) in AST or ALT levels in the plasma, whereas a slight, yet significant (P<0.001) 3 to 4-fold increase in AST and ALT levels was apparent one day following Ad-AAT-cFVIII transduction compared to PBS-injected controls. Nevertheless, after a few days AST and ALT levels returned to basal levels undistinguishable from normal physiologic levels. The exact reason for the differences among the different vector batches is not clear but might potentially reflect differences in vector purity. Since administration of early-generation adenoviral vectors is known to result in thrombocytopenia (see, Cichon G, Schmidt H H, Benhidjeb T, Loser P, Ziemer S, Haas R, Grewe N, Schnieders F, Heeren J, Manns M P, Schlag P M, Strauss M. Intravenous administration of recombinant adenoviruses causes thrombocytopenia, anemia and erythroblastosis in rabbits. J Gene Med. 1999, 1:360-371), platelets were counted in FVIIIKO mice that had received $5 \times 10^9$ i.u. of Ad-AAT-cFVIII, Ad-AAT-hFVIII and Ad-Apo-cFVIII. No significant differences in platelet counts were observed in mice that received the different HC-Ad vectors compared to PBS-injected FVIIIKO controls (FIG. 7B). In addition, there was no evidence of anemia or erythroblastosis since erythrocyte counts were normal following HC-Ad vector administration in FVIIIKO mice. Finally, it has been shown that early-generation adenoviral vectors trigger a rapid induction of pro-inflammatory cytokines, particularly IL-6, which is associated with an acute phase inflammatory response that contributes to vector toxicity (see, Lieber A, He C Y, Meuse L, Schowalter D, Kirillova I, Winther B, Kay M A. The role of Kupffer cell activation and viral gene expression in early liver toxicity after infusion of recombinant adenovirus vectors. J Virol. 1997; 71:8798-8807). To determine whether the vectors used in this study were associated with an upregulation of IL-6, FVIIIKO mice were injected with $5 \times 10^9$ i.u. of Ad-AAT-cFVIII, Ad-AAT-hFVIII and Ad-Apo-cFVIII (FIG. 7C). As in control animals, there were no significant increases (1-way ANOVA P>0.05) in plasma IL-6 levels following injection of the various HC-Ad vectors. In conclusion, these results underscore the relative safety of HC-Ad vectors for gene therapy of hemophilia A.

EXAMPLE 8

Application of the Recombinant HC-adenoviral Vector in Hemophilic Dogs $5.6 \times 10^{10}$ infectious units (i.u.) of the HCAd-Apo-FVIIIDB vector were intraveneously injected into a 13 kg adult 6 year old dog (homozygous FVIII-deficient female) with severe hemophilia A (hemophilia A dog colony, Queens University, Kingston, Ontario, Canada) (Hough et al., Thromb Haemost. 2002 April; 87(4):659-65). This corresponds to a total vector dose of $4 \times 10^{12}$ vector particles (v.p.) per dog. Alternatively, the actual dose per kg is $4.3 \times 10^9$ i.u./kg or $3 \times 10^{11}$ v.p./kg. The v.p./i.u. ratio is somewhat higher in this vector batch v.p./i.u.=70 compared to the vector batch used in the hemophilic mice (example 2): v.p./i.u.=30). A dose of $4.3 \times 10^9$ i.u./kg in a mouse of about 30 g would therefore be equivalent to a low dose of only $1.4 \times 10^8$ i.u. per mouse. The whole blood clotting time (WBCT) of the hemophilic dog prior to treatment was about 15 min and after injection of the HCAd-Apo-FVIIIDB vector resulted in a decrease of the WBCT to 7-9 min as early as 72 hr post-injection consistent with a phenotypic correction of the bleeding disorder. The dog displayed normal activity after injection, with no visible side-effects which are known to occur following adenoviral gene transfer. In particular, there were no signs of fever, lethargy, cyanosis or nausea. This confirms the relative safety and efficacy of these improved HC-Ad-FVIIIDB vectors for gene therapy of hemophilia A in a large clinically relevant hemophilic animal model that mimics the cognate human disease.

Materials and Methods

Construction of the B-domain Deleted FVIII cDNA

The human B-domain deleted FVIII cDNA was generated by PCR cloning starting from pSP64-FVIII clone, which was originally obtained from the American Type Culture Collection (Rockville, Md., USA) containing the full-length FVIII cDNA. This particular human B-domain deleted FVIII cDNA had several unique features that were intended to increase gene expression. A Kozak translational consensus was included to increase translational efficiency. A more efficient TAA stop codon was used instead of a TGA. In addition, the 3' untranslated region (UTR) was deleted, since it may inhibit gene expression (see, Gallo-Penn A M, Shirley P S, Andrews J L, Kayda D B, Pinkstaff A M, Kaloss M, Tinlin S, Cameron C, Notley C, Hough C, Lillicrap D, Kaleko M, Connelly S. In vivo evaluation of an adenoviral vector encoding canine factor VIII: high-level, sustained expression in hemophiliac mice. Hum Gene Ther. 1999, 10:1791-1802). The B-domain deletion starts at amino acid 741 (Ser), hereby retaining the 740 thrombin cleavage site, until amino acid 1668 (Ile), hereby retaining the thrombin and Xa cleavage sites at position 1689 (Arg) and the putative vWF binding site between 1670 (Val)-1689 (Arg). This 4.3 kb B-domain deleted FVIII was reported to have the same activity as plasma-derived FVIII (see, Mertens K, Donath M J, van Leen R W, de Keyzer-Nellen M J, Verbeet M P, Klaasse Bos J M, Leyte A, van Mourik J A. Biological activity of recombinant factor VIII variants lacking the central B-domain and the heavy-chain sequence Lys713-Arg740: discordant in vitro and in vivo activity. Br J Haematol. 1993, 85:133-142). The 4.4 kb canine B-domain deleted FVIII cDNA sequence has been described previously (Cameron C, Notley C, Hoyle S, McGlynn L, Hough C, Kamisue S, Giles A, Lillicrap D. The canine factor VIII cDNA and 5' flanking sequence. Thromb Haemost. 1998, 79:317-322).

Vector Construction

The HC-Ad vectors Ad-AAT-cFVIII, Ad-AAT-hFVIII and Ad-Apo-cFVIII were constructed as infectious plasmids (pAd-AAT-cFVIII, pAd-AAT-hFVIII, and pAd-Apo-cFVIII (deposited on Sep. 2, 2004, under Accession number LMBP 4934 at the Belgian Coordinated Collections of Microorganisms-BCCM™, Laboratorium voor Moleculaire Biolgies-Plasmidencollectie (LMBP) Universiteit Gent, Technolgiepark 927, B-9052 Gent-Zwijnaarde, Belgium). Schematic structures of the different plasmids are shown in FIGS. 1A and 1B. The plasmid for construction of Ad-AAT-cFVIII vector (pVB8) contains the Ad5 left terminus (nt. 1-440), a 12 kb genomic fragment from the human alfa1-antitrypsin (AAT) locus (embedding the liver and macrophage-specific promoter, the first AAT exon and intron, and the splice acceptor of the second exon), a unique EcoRV restriction site, beta-globin poly A, HPRT stuffer (nt. 17855-14588, nt. 8563-1799), and the Ad5 right terminus (nt. 35818-35935).

The canine FVIII cDNA (B-domain deleted) was excised with XbaI and SmaI from plasmid pBKCMVmun2bdd1-6 and introduced into the EcoRV site of the above described plasmid pVB8 resulting in pAd-AAT-cFVIII. The human FVIII cDNA (B-domain deleted) was excised with SalI and NotI from plasmid pBIISKF8 clone 81 and introduced into the EcoRV site of the above described plasmid resulting in pAd-AAT-hFVIII (FIG. 1A). The plasmid for construction of Ad-Apo-cFVIII vector (pFK2) contains the Ad5 left terminus (nt. 1-440), HPRT stuffer (nt. 1799-21729), SV40 poly A, a unique NotI site, hCMV promoter, the chimeric ApoE-ApoCII promoter (Apo), C346 stuffer (nt. 10205-16750, including a unique Eco47III site), and the Ad5 right terminus (nt. 35818-35935). The ApoE-ApoCII hybrid promoter already joined to the canine FVIII cDNA (B-domain deleted) was excised with ClaI and SmaI from plasmid PRRLsinPPTs.AE4.CF8.preEcoXma and introduced into plasmid pFK2 cleaved with NotI and Eco47III. In the resulting plasmid pAd-Apo-cFVIII the hCMV promoter plus sequences from the C346 stuffer sequences were deleted (FIG. 1B).

Rescue of HC-Ad Vectors

Plasmids pAd-AAT-cFVIII pAd-AAT-hFVIII, and pAd-Apo-cFVIII were digested with PmeI flanking the adenoviral termini, phenol/chloroform extracted and precipitated with ethanol. Two micrograms of each plasmid were transfected into 293-based Cre66 cells (Schiedner et al., manuscript in preparation), which were coinfected with the loxP helper virus AdLC8cluc (Parks R J, Chen L, Anton M, Sankar U, Rudnicki M A, Graham F L. A helper-dependent adenovirus vector system: removal of helper virus by Cre-mediated excision of the viral packaging signal. Proc Natl Acad Sci USA. 1996, 93:13565-13570). Subsequent amplification steps and large scale preparation were performed as described previously. All vector preparation were purified twice by CsCl equilibrium density centrifugation and the particle titers were evaluated by optical density measurements.

Animal Studies

FVIII-deficient mice containing a disruption of the murine FVIII gene (Bi L, Lawler A M, Antonarakis S E, High K A, Gearhart J D, Kazazian H H, Jr. Targeted disruption of the mouse factor VIII gene produces a model of haemophilia A [letter]. Nat Genet. 1995, 10:119-121) were bred to generate homozygous FVIII-deficient females and hemizygous FVIII-deficient males (designated as FVIIIKO). To obtain immunodeficient hemophilic mice (designated as FVIIIKO-SCID), FVIII-deficient mice were crossed with SCID mice (Bosma G C, Custer R P, Bosma M J. A severe combined immunodeficiency mutation in the mouse. Nature. 1983, 301:527-530). These SCID mice are characterized by a severe combined immune deficiency and are unable to mount a specific immune response to foreign antigens due to the lack of functional T and B-cells. Genotyping and phenotypic characterization of the FVIIIKO and FVIIIKO-SCID offspring was performed as described (Bi et al. 1995, supra) confirming that all FVIII-deficient mice used in this study contained the disrupted murine FVIII gene. Two- to three months old FVIIIKO or FVIIIKO-SCID mice were injected intravenously via the tail vein with the Ad-AAT-cFVIII, Ad-AAT-hFVIII or Ad-Apo-cFVIII HC-Ad vector constructs at a dose of $5 \times 10^9$ infectious units (i.u.) per mouse. A dose response study was performed with the Ad-AAT-cFVIII vector at doses of $5 \times 10^9$, $10^9$, $5 \times 10^8$ and $10^8$ i.u. per mouse. Similarly, FVIII-deficient littermates were injected with PBS as a control. Plasma samples were obtained from each mouse by retro-orbital bleeding in 20% 0.1 M sodium citrate for functional human or canine FVIII determination, for measuring cytokine and aminotransferase levels and for Bethesda assays. Experiments were approved by the Animal Ethical Commission of the University of Leuven.

Analysis of FVIII Production and Anti-FVIII Antibodies

Biologically active human and canine FVIII was quantified in citrate-containing plasma samples from FVIIIKO or FVIIIKO-SCID mice by using FVIII COAtests (Chromogenix, Molndal, Sweden) (see, Chuah M K, Vandendriessche T, Morgan R A. Development and analysis of retroviral vectors expressing human factor VIII as a potential gene therapy for hemophilia A. Hum Gene Ther. 1995, 6:1363-1377). Plasma from FVIIIKO or FVIIIKO-SCID mice spiked with human plasma derived FVIII (Octapharma, Langenfeld, Germany) of known activity was used as standard. One unit corresponded to 200 ng FVIII/ml (100%). The sensitivity of the assay was about 20-30 mU/ml. Physiologic FVIII concentrations were defined as 200 ng/ml. To further assess phenotypic correction of the clotting deficiency, plasma samples were subjected to a functional clotting assay (aPTT) that measures the activated partial thromboplastin time (Hemoliance SythASil APTT Reagent, Lexington, Mass., USA). The inhibitory antibody titers were determined with Bethesda assays as described (Kasper C K, Aledort L, Aronson D, Counts R, Edson J R, van Eys J, Fratantoni J, Green D, Hampton J, Hilgartner M, Levine P, Lazerson J, McMillan C, Penner J, Shapiro S, Shulman N R. Proceedings: A more uniform measurement of factor VIII inhibitors. Thromb Diath Haemorrh. 1975, 34:612). Briefly, inhibition of FVIII activity by serially diluted mouse plasma was measured by using a functional FVIII COAtest. The detection limit of the assay was 0.2-0.4 Bethesda units/ml.

Macrophage Depletion Study

Transient depletion of macrophages in liver and spleen of FVIIIKO and FVIIIKO-SCID mice was performed by intravenously injecting 0.2 ml of clodronate-containing liposomes (Van Rooijen N, Sanders A. Kupffer cell depletion by liposome-delivered drugs: comparative activity of intracellular clodronate, propamidine, and ethylenediaminetetraacetic acid. Hepatology. 1996, 23:1239-1243) 24 hr prior to injection of different doses of Ad-AAT-cFVIII vector ranging from $10^8$ i.u. to $5 \times 10^6$ i.u. Clodronate was a gift of Roche Diagnostics GmbH (Mannheim, Germany). Phospatidylcholine (Lipiod E PC) (Lipiod GmbH, Ludwigshafen, Germany) and cholesterol (Sigma, USA) was used to prepare the liposomes. Littermates were injected with liposomes containing PBS as controls. To confirm the effectiveness of the macrophage depletion, some mice were sacrificed and single-cell suspensions were prepared from liver and spleen that were subsequently analyzed by flow cytometry (FACSCalibur™, equipped with CELLquest software, Becton Dickinson, Sunnyvale, Calif., USA) using PE-conjugated macrophage-specific antibodies including anti-MHC class II antibodies (BD Phamingen, Belgium) and antibodies specific for the F4/80 macrophage marker (Serotec, Belgium). Appropriate isotype-matched control antibodies were included in the FACS analysis.

Analysis of Vector DNA and RNA in vivo

FVIIIKO mice were injected with $5 \times 10^9$ i.u. of Ad-AAT-hFVIII. Genomic DNA from different organs was extracted by phenol/chloroform extraction as described previously (VandenDriessche T, Vanslembrouck V, Goovaerts I, Zwinnen H, Vanderhaeghen M L, Collen D, Chuah M K. Long-term expression of human coagulation factor VIII and correction of hemophilia A after in vivo retroviral gene transfer in factor VIII-deficient mice [see comments]. Proc Natl Acad Sci USA. 1999, 96:10379-10384). Polymerase chain reaction (PCR) with human FVIII-specific primers (5'-CCATATAACATCTACCCTCA-3' (SEQ ID NO 1) and 5'-GTTTCTCCTGAGAATGGGAA-3' (SEQ ID NO 2)) was used to detect HC-Ad FVIII DNA. PCR was performed using PlatinumTaq (Invitrogen, Merelbeke, Belgium) by denaturing for 2 min at 94° C., followed by 30 cycles of 30 sec at 94° C., 30 sec at 55° C., 1 min at 72° C.), yielding a 0.6 kb fragment. A retrovirally transduced vector producer cell line with a known number of human FVIII gene copies served as the standard (see, Ibid. and Chuah M K, Brems H, Vanslembrouck V, Collen D, Vandendriessche T. Bone marrow stromal cells as targets for gene therapy of hemophilia A. Hum Gene Ther. 1998; 9, 353-365) for comparison. For normalization, a PCR with -actin specific primers was performed as described previously yielding a 0.2 kb fragment. Reverse transcription-PCR (RT-PCR) was performed as described previously (see, VandenDriessche et al. 1999, supra) and the PCR conditions and primers were identical to those mentioned above.

Toxicity Studies

Plasma measurements of serum alanine aminotransferase (ALT) and aspartate aminotransferase (AST) levels were performed on a Modular System (Roche/Hitachi) according to the manufacturer's instructions. Plasma samples were obtained from FVIIIKO-SCID mice (n=3) injected with $5\times10^9$ i.u. Ad-AAT-cFVIII, Ad-AAT-hFVIII and Ad-Apo-cFVIII vectors. The plasma levels of the pro-inflammatory cytokine IL-6 were determined after injection of $5\times10^9$ i.u. Ad-AAT-cFVIII, Ad-AAT-hFVIII and Ad-Apo-cFVIII vectors into FVIIIKO mice with a sandwich ELISA (Quantikine, R&D Systems, Inc., Minneapolis, USA). Thrombocytes and erythrocytes in FVIIIKO mice injected with $5\times10^9$ i.u. Ad-AAT-cFVIII, Ad-AAT-hFVIII and Ad-Apo-cFVIII vectors were measured in total blood containing 10% EDTA using a Cell-dyn 1300 blood counter (Abbott, Ill., USA).

It will be apparent that details of the vectors and methods herein described can be varied considerably without departing from the concept and scope of the invention. The claims alone define the scope of the invention as conceived and as described herein.

REFERENCES

1. Kaufman R J. Advances toward gene therapy for hemophilia at the millennium. Hum Gene Ther. 1999; 10:2091-2107
2. Kay M A, High K. Gene therapy for the hemophilias [comment]. Proc Natl Acad Sci USA. 1999; 96:9973-9975
3. Chuah M K, Collen D, VandenDriessche T. Gene therapy for hemophilia: hopes and hurdles. Crit Rev Oncol Hematol. 1998; 28:153-171
4. Chuah M K, Collen D, VandenDriessche T. Gene therapy for hemophilia. J Gene Med. 2001; 3:3-20.
5. Yang Y, Su Q, Wilson J M. Role of viral antigens in destructive cellular immune responses to adenovirus vector-transduced cells in mouse lungs. J Virol. 1996; 70:7209-7212
6. Fang B, Wang H, Gordon G, Bellinger D A, Read M S, Brinkhous K M, Woo S L, Eisensmith R C. Lack of persistence of E1-recombinant adenoviral vectors containing a temperature-sensitive E2A mutation in immunocompetent mice and hemophilia B dogs. Gene Ther. 1996; 3:217-222
7. Schiedner G, Morral N, Parks R J, Wu Y, Koopmans S C, Langston C, Graham F L, Beaudet A L, Kochanek S. Genomic DNA transfer with a high-capacity adenovirus vector results in improved in vivo gene expression and decreased toxicity [published erratum appears in Nat Genet 1998 March; 18(3):298]. Nat Genet. 1998; 18:180-183
8. Yang Y, Ertl H C, Wilson J M. MHC class I-restricted cytotoxic T lymphocytes to viral antigens destroy hepatocytes in mice infected with E1-deleted recombinant adenoviruses. Immunity. 1994; 1:433-442
9. Yang Y, Li Q, Ertl H C, Wilson J M. Cellular and humoral immune responses to viral antigens create barriers to lung-directed gene therapy with recombinant adenoviruses. J Virol. 1995; 69:2004-2015
10. Yang Y, Jooss K U, Su Q, Ertl H C, Wilson J M. Immune responses to viral antigens versus transgene product in the elimination of recombinant adenovirus-infected hepatocytes in vivo. Gene Ther. 1996; 3:137-144
11. Connelly S, Smith T A, Dhir G, Gardner J M, Mehaffey M G, Zaret K S, McClelland A, Kaleko M. In vivo gene delivery and expression of physiological levels of functional human factor VIII in mice. Hum Gene Ther. 1995; 6:185-193
12. Connelly S, Gardner J M, McClelland A, Kaleko M. High-level tissue-specific expression of functional human factor VIII in mice. Hum Gene Ther. 1996; 7:183-195
13. Connelly S, Mount J, Mauser A, Gardner J M, Kaleko M, McClelland A, Lothrop C D, Jr. Complete short-term correction of canine hemophilia A by in vivo gene therapy. Blood. 1996; 88:3846-3853
14. Connelly S, Andrews J L, Gallo A M, Kayda D B, Qian J, Hoyer L, Kadan M J, Gorziglia M I, Trapnell B C, McClelland A, Kaleko M. Sustained phenotypic correction of murine hemophilia A by in vivo gene therapy. Blood. 1998; 91:3273-3281
15. Gallo-Penn A M, Shirley P S, Andrews J L, Tinlin S, Webster S, Cameron C, Hough C, Notley C, Lillicrap D, Kaleko M, Connelly S. Systemic delivery of an adenoviral vector encoding canine factor VIII results in short-term phenotypic correction, inhibitor development, and biphasic liver toxicity in hemophilia A dogs. Blood. 2001; 97:107-113.
16. Kochanek S. High-capacity adenoviral vectors for gene transfer and somatic gene therapy. Hum Gene Ther. 1999; 10:2451-2459
17. Parks R J, Chen L, Anton M, Sankar U, Rudnicki M A, Graham F L. A helper-dependent adenovirus vector system: removal of helper virus by Cre-mediated excision of the viral packaging signal. Proc Natl Acad Sci USA. 1996; 93:13565-13570
18. Gallo-Penn A M, Shirley P S, Andrews J L, Kayda D B, Pinkstaff A M, Kaloss M, Tinlin S, Cameron C, Notley C, Hough C, Lillicrap D, Kaleko M, Connelly S. In vivo evaluation of an adenoviral vector encoding canine factor VIII: high-level, sustained expression in hemophiliac mice. Hum Gene Ther. 1999; 10:1791-1802
19. Mertens K, Donath M J, van Leen R W, de Keyzer-Nellen M J, Verbeet M P, Klaasse Bos J M, Leyte A, van Mourik J A. Biological activity of recombinant factor VIII variants lacking the central B-domain and the heavy-chain sequence Lys713-Arg740: discordant in vitro and in vivo activity. Br J Haematol. 1993; 85:133-142.
20. Cameron C, Notley C, Hoyle S, McGlynn L, Hough C, Kamisue S, Giles A, Lillicrap D. The canine factor VIII cDNA and 5' flanking sequence. Thromb Haemost. 1998; 79:317-322
21. Bi L, Lawler A M, Antonarakis S E, High K A, Gearhart J D, Kazazian H H, Jr. Targeted disruption of the mouse factor VIII gene produces a model of haemophilia A [letter]. Nat Genet. 1995; 10:119-121
22. Bosma G C, Custer R P, Bosma M J. A severe combined immunodeficiency mutation in the mouse. Nature. 1983; 301:527-530
23. Chuah M K, Vandendriessche T, Morgan R A. Development and analysis of retroviral vectors expressing human factor VIII as a potential gene therapy for hemophilia A. Hum Gene Ther. 1995; 6:1363-1377
24. Kasper C K, Aledort L, Aronson D, Counts R, Edson J R, van Eys J, Fratantoni J, Green D, Hampton J, Hilgartner M, Levine P, Lazerson J, McMillan C, Penner J, Shapiro S, Shulman N R. Proceedings: A more uniform measurement of factor VIII inhibitors. Thromb Diath Haemorrh. 1975; 34:612
25. Van Rooijen N, Sanders A. Kupffer cell depletion by liposome-delivered drugs: comparative activity of intracellular clodronate, propamidine, and ethylenediaminetetraacetic acid. Hepatology. 1996; 23:1239-1243.
26. VandenDriessche T, Vanslembrouck V, Goovaerts I, Zwinnen H, Vanderhaeghen M L, Collen D, Chuah M K. Long-term expression of human coagulation factor VIII and correction of hemophilia A after in vivo retroviral gene transfer in factor VIII-deficient mice [see comments]. Proc Natl Acad Sci USA. 1999; 96:10379-10384
27. Chuah M K, Brems H, Vanslembrouck V, Collen D, Vandendriessche T. Bone marrow stromal cells as targets for gene therapy of hemophilia A. Hum Gene Ther. 1998; 9:353-365
28. Parks R J, Graham F L. A helper-dependent system for adenovirus vector production helps define a lower limit for efficient DNA packaging. J Virol. 1997; 71:3293-3298
29. Morral N, O'Neal W, Rice K, Leland M, Kaplan J, Piedra P A, Zhou H, Parks R J, Velji R, Aguilar-Cordova E, Wadsworth S, Graham F L, Kochanek S, Carey K D, Beaudet A L. Administration of helper-dependent adenoviral vectors and sequential delivery of different vector serotype for long-term liver-directed gene transfer in baboons. Proc Natl Acad Sci USA. 1999; 96:12816-12821
30. Schiedner G, Hertel S, Johnston M, Biermann V, Dries V, Kochanek S. Variables affecting in vivo performance of high-capacity adenovirus vectors. J Virol. 2002; 76:1600-1609.
31. Pastore L, Morral N, Zhou H, Garcia R, Parks R J, Kochanek S, Graham F L, Lee B, Beaudet A L. Use of a liver-specific promoter reduces immune response to the transgene in adenoviral vectors. Hum Gene Ther. 1999; 10:1773-1781
32. Lozier J N, Metzger M E, Donahue R E, Morgan R A. Adenovirus-mediated expression of human coagulation factor IX in the rhesus macaque is associated with dose-limiting toxicity [see comments]. Blood. 1999; 94:3968-3975
33. Cichon G, Schmidt H H, Benhidjeb T, Loser P, Ziemer S, Haas R, Grewe N, Schnieders F, Heeren J, Manns M P, Schlag P M, Strauss M. Intravenous administration of recombinant adenoviruses causes thrombocytopenia, anemia and erythroblastosis in rabbits. J Gene Med. 1999; 1:360-371.
34. Lieber A, He C Y, Meuse L, Schowalter D, Kirillova I, Winther B, Kay M A. The role of Kupffer cell activation and viral gene expression in early liver toxicity after infusion of recombinant adenovirus vectors. J Virol. 1997; 71:8798-8807
35. Balague C, Zhou J, Dai Y, Alemany R, Josephs S F, Andreason G, Hariharan M, Sethi E, Prokopenko E, Jan H Y, Lou Y C, Hubert-Leslie D, Ruiz L, Zhang W W. Sustained high-level expression of full-length human factor VIII and restoration of clotting activity in hemophilic mice using a minimal adenovirus vector. Blood. 2000; 95:820-828
36. Chao H, Mao L, Bruce A T, Walsh C E. Sustained expression of human factor VIII in mice using a parvovirus-based vector. Blood. 2000; 95:1594-1599
37. Park F, Ohashi K, Kay M A. Therapeutic levels of human factor VIII and IX using HIV-1-based lentiviral vectors in mouse liver. Blood. 2000; 96:1173-1176
38. Evans G L, Morgan R A. Genetic induction of immune tolerance to human clotting factor VIII in a mouse model for hemophilia A. Proc Natl Acad Sci USA. 1998; 95:5734-5739
39. Chuah M K, Van Damme A, Zwinnen H, Goovaerts I, Vanslembrouck V, Collen D, Vandendriessche T. Long-term persistence of human bone marrow stromal cells transduced with factor VIII-retroviral vectors and transient production of therapeutic levels of human factor VIII in nonmyeloablated immunodeficient mice. Hum Gene Ther. 2000; 11:729-738
40. Pittman D D, Alderman E M, Tomkinson K N, Wang J H, Giles A R, Kaufman R J. Biochemical, immunological, and in vivo functional characterization of B-domain-deleted factor VIII. Blood. 1993; 81:2925-2935
41. Connelly S, Andrews J L, Gallo-Penn A M, Tagliavacca L, Kaufman R J, Kaleko M. Evaluation of an adenoviral vector encoding full-length human factor VIII in hemophiliac mice. Thromb Haemost. 1999; 81:234-239
42. Morsy M A, Gu M, Motzel S, Zhao J, Lin J, Su Q, Allen H, Franlin L, Parks R J, Graham F L, Kochanek S, Bett A J, Caskey C T. An adenoviral vector deleted for all viral coding sequences results in enhanced safety and extended expression of a leptin transgene. Proc Natl Acad Sci USA. 1998; 95:7866-7871
43. Barrera P, Blom A, van Lent P L, van Bloois L, Beijnen J H, van Rooijen N, de Waal Malefijt M C, van de Putte L B, Storm G, van den Berg W B. Synovial macrophage depletion with clodronate-containing liposomes in rheumatoid arthritis. Arthritis Rheum. 2000; 43:1951-1959.

What is claimed is:

1. A recombinant high capacity adenoviral vector comprising:
    an Ad5 left terminus;
    a human or canine Factor VIII cDNA under the control of a chimeric ApoE/ApoCII promoter, wherein the B-domain of the Factor VIII cDNA has been deleted; and
    an Ad5 right terminus.

2. A method to obtain therapeutic levels of Factor VIII in a mammal comprising:
    administering less than $10^{10}$ infectious units of a recombinant high capacity adenoviral vector per kg of body weight or less than $10^{12}$ viral particles of the recombinant high capacity adenoviral vector per kg of body weight intravenously to the mammal's liver;
    wherein the recombinant high capacity adenoviral vector comprises:
        an Ad5 left terminus;
        a human or canine Factor VIII cDNA under the control of a liver specific promoter, wherein the B-domain of the Factor VIII cDNA has been deleted; and
        an Ad5 right terminus.

3. The method according to claim 2, wherein said mammal is a dog or a human.

4. A method of treating hemophilia A in a mammal, comprising:
    administering less than $10^{10}$ infectious units of a recombinant high capacity adenoviral vector per kg of body weight or less than $10^{12}$ viral particles of the recombinant high capacity viral vector per kg of body weight intravenously to the mammal's liver, said recombinant high capacity adenoviral vector comprising:
        an Ad5 left terminus;
        a human or canine Factor VIII cDNA under the control of a liver specific promoter, wherein the B-domain of the Factor VIII cDNA has been deleted; and
        an Ad5 right terminus;
    thus generating therapeutic amounts of Factor VIII in said mammal to substantially ameliorate the effects of hemophilia A.

5. The method according to claim 4, wherein said mammal is a dog or a human.

* * * * *

UNITED STATES PATENT AND TRADEMARK OFFICE
CERTIFICATE OF CORRECTION

PATENT NO. : 7,238,346 B2
APPLICATION NO. : 10/191760
DATED : July 3, 2007
INVENTOR(S) : Thierry Vandendriessche et al.

It is certified that error appears in the above-identified patent and that said Letters Patent is hereby corrected as shown below:

On the title page:
In ITEM (56) References Cited
OTHER PUBLICATIONS change "Gallo-Penn et al., "Systemic delivery of an adenoviral vecotr" to --Gallo-Penn et al., "Systemic delivery of an adenoviral vector--
change "resoration of clotting activity in hemophiliac mice" to --restoration of clotting activity in hemophiliac mice--
change "canine model of severe hemophilia" to --canine model for severe hemophilia--

Signed and Sealed this

Sixteenth Day of December, 2008

JON W. DUDAS
*Director of the United States Patent and Trademark Office*